US009283396B2

(12) United States Patent
Janzig

(10) Patent No.: US 9,283,396 B2
(45) Date of Patent: Mar. 15, 2016

(54) IMPLANTABLE DEVICE WITH SHIELD INTEGRATED LEAD CONNECTOR

(71) Applicant: MEDTRONIC, INC., Minneapolis, MN (US)

(72) Inventor: Darren A. Janzig, Center City, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/210,901

(22) Filed: Mar. 14, 2014

(65) Prior Publication Data

US 2014/0277218 A1 Sep. 18, 2014

Related U.S. Application Data

(60) Provisional application No. 61/789,279, filed on Mar. 15, 2013.

(51) Int. Cl.
*A61N 1/375* (2006.01)

(52) U.S. Cl.
CPC .................................. *A61N 1/3752* (2013.01)

(58) Field of Classification Search
CPC .............. A61N 1/3752; A61N 1/3605; A61N 1/36125; A61N 1/3754; H01R 13/5224; A61B 17/3468
See application file for complete search history.

(56) References Cited

U.S. PATENT DOCUMENTS

| 4,262,982 | A |  | 4/1981 | Kenny |
|---|---|---|---|---|
| 4,934,366 | A |  | 6/1990 | Truex |
| 5,906,634 | A | * | 5/1999 | Flynn et al. ..................... 607/37 |
| 7,515,964 | B1 |  | 4/2009 | Alexander |
| 7,563,141 | B2 |  | 7/2009 | Alexander |
| 7,711,427 | B2 |  | 5/2010 | Janzig |
| 7,711,428 | B2 |  | 5/2010 | Janzig |
| 7,890,175 | B1 |  | 2/2011 | Rey |
| 8,131,370 | B2 |  | 3/2012 | Janzig |
| 8,738,141 | B2 |  | 5/2014 | Smith |
| 2007/0179553 | A1 |  | 8/2007 | Iyer |
| 2011/0004229 | A1 |  | 1/2011 | Priplata |
| 2011/0065301 | A1 | * | 3/2011 | Boyd et al. ..................... 439/271 |
| 2014/0277216 | A1 |  | 9/2014 | Janzig |
| 2014/0277217 | A1 |  | 9/2014 | Janzig |

FOREIGN PATENT DOCUMENTS

EP          11246101  B1     7/2004

* cited by examiner

*Primary Examiner* — Rex R Holmes
(74) *Attorney, Agent, or Firm* — Mueting, Raasch & Gebhardt, P.A.

(57) ABSTRACT

An implantable active medical device includes a hermetic housing defining an exterior surface and a hermetic cavity of an implantable active medical device. The hermetic housing has a first major surface, an opposing second major surface and a side surface extending between them. An elongate lead connector is recessed into the first major surface. The elongate lead connector has a top surface and a bottom surface and a side surface extending between them. The top surface forms only a portion of the first major surface.

20 Claims, 4 Drawing Sheets

IMPLANTABLE DEVICE WITH SHIELD INTEGRATED LEAD CONNECTOR

CROSS-REFERENCE

This application claims the benefit of U.S. Provisional Application Ser. No. 61/789,279, filed Mar. 15, 2013, the disclosure of which is incorporated herein by reference.

BACKGROUND

Implantable active medical devices, such as cardiac rhythm management devices (pacemakers and defibrillators) and a variety of implantable muscle/nerve stimulators, for example, generally include a battery and battery-powered electronic pulse generator contained within a hermetically sealed housing or case and attached to a lead connector housing or block. The hermetically sealed housing most often comprises one or more device shields (also known as shields) and may include a header plate all hermetically joined to form a hermetic cavity. The lead connector block (may also be known as connector header) is often affixed to the hermetically sealed housing with brackets, metal solder, laser or resistance welding, pins, screws, fasteners and/or a medical grade adhesive. The method of fixation requires extensive design and load testing to ensure adequate fixation. The function of the lead connector block is to electrically and mechanically couple the electronic pulse generator with the therapy lead. The lead connector block is typically attached to the exterior of the hermetically sealed housing and is significant to defining the overall device shape and volume. Most often with each new device design, a new lead connector block must also be designed requiring substantial project resources and project schedule.

The electronics within the hermetically sealed housing are conductively coupled to the lead connector block via an electrical feedthrough assembly. Electrical feedthroughs serve the purpose of providing a conductive path extending between the interior of a hermetically sealed container and a point outside the hermetically sealed housing that ultimately connects to the electrical contacts that interface with the therapy lead connector rings. The conductive path through the feedthrough usually includes a conductor pin or terminal that is electrically insulated from the hermetically sealed housing and hermetically bonded to a feedthrough housing or ferrule. The feedthrough housing is hermetically assembled to the device housing most often by laser welding. While this arrangement has proven to be highly reliable, it involves a variety of expensive manufacturing processes and parts that necessarily increase the cost and overall volume of the resulting product and limit device shape or configuration.

Ongoing efforts by the industry to reduce the size of the implantable device are desired. Early implantable pacemakers back in the 1960's were about the size of a hockey puck. With advances in microelectronics and integrated circuitry, significantly more features and capabilities have been embodied in implantable active medical devices that can be very small. Nonetheless, efforts to further reduce the size of implantable active medical devices continue in the industry.

BRIEF SUMMARY

The present disclosure relates to an implantable medical device having a hermetic housing with a shield integrated lead connector. In particular the present disclosure relates to an elongate lead connector recessed or embedded into a top major surface of the implantable medical device.

In one illustrative embodiment, an implantable active medical device includes a hermetic housing defining an exterior surface and a hermetic cavity of an implantable active medical device. The hermetic housing has a first major surface, an opposing second major surface and a side surface extending between them. An elongate lead connector is recessed into the first major surface. The elongate lead connector has a top surface and a bottom surface and a side surface extending between them. The top surface forms only a portion of the first major surface of the hermetic housing.

In another illustrative embodiment, an implantable active medical device includes a hermetic housing defining an exterior surface and a hermetic cavity of an implantable active medical device. The hermetic housing has a first major surface, an opposing second major surface and a side surface extending between the first major surface and the second major surface. An elongate lead connector is embedded into the first major surface. The elongate lead connector has a top surface and a bottom surface and opposing longitudinal side surfaces extending between the top surface and the bottom surface. The lead connector also has a closed end rear surface extending between the top surface and the bottom surface and the opposing longitudinal side surfaces, and an open end front surface opposing the rear surface and defining a lead aperture and extending between the top surface and the bottom surface and the opposing longitudinal side surfaces. The hermetic cavity surrounds the opposing longitudinal side surfaces and the closed end rear surface.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
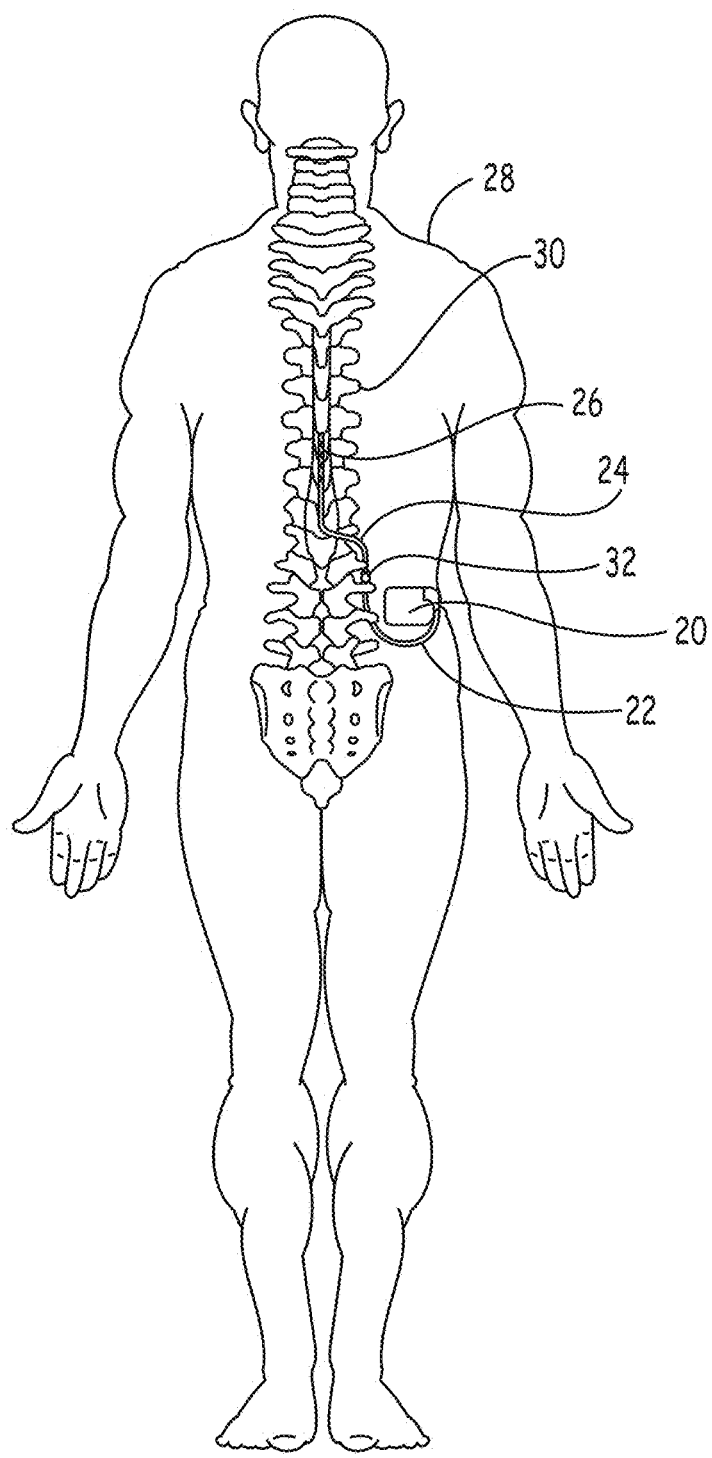
FIG. 1 is a schematic diagram of a an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "top", bottom", "front", "rear", "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to an implantable medical device having a hermetic housing with a shield integrated lead connector. In particular the present disclosure relates to an elongate lead connector recessed or embedded into a top major surface of the implantable medical device (known as the device shield). The elongate lead connector can have a bottom surface that is disposed on a major surface of the circuit board where the elongate lead connector extends orthogonally away from the major surface of the circuit board. The hermetic housing can envelope or surround all sides of the elongate lead connector except for the top surface and an open lead aperture end. The top surface of the elongate lead connector can be transparent so that a user can confirm positive engagement of any therapy lead body in the elongate lead connector. While the present disclosure is not so limited, an appreciation of various aspects of the disclosure will be gained through a discussion of the examples provided below.

FIG. 1 is a schematic diagram of an active medical device 20 implanted within a human body of patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30.

In many embodiments, the active medical device 20 has one or two leads each having four to eight electrodes or more electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

In many embodiments, each lead 24 is a wire having insulation thereon and includes one or more insulated electrical conductors each coupled at their proximal end to a connector ring and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). In some embodiments, each lead 24 may contain a paddle shape at its distant end for housing electrodes 26. In many embodiments, electrodes 26 may include one or more ring electrodes at the distal end of the lead 24.

Figure 2:
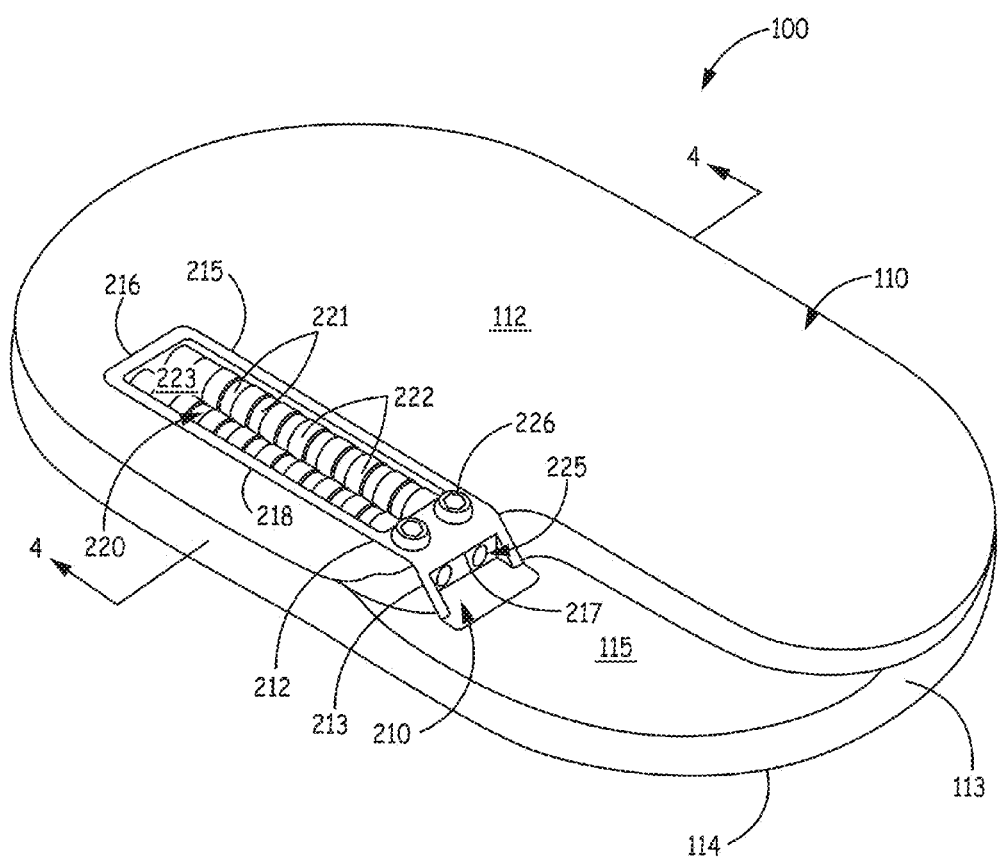
FIG. 2 is a schematic perspective view of an illustrative implantable active medical device with the elongate lead connector recessed or embedded in a first major surface of the hermetic housing.
Figure 3:
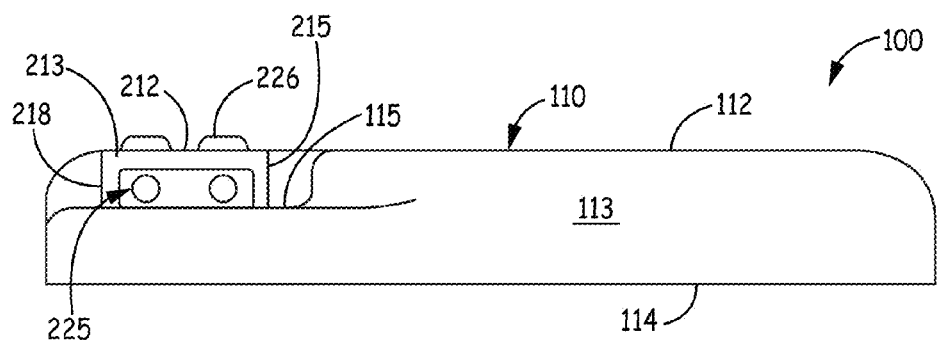
FIG. 3 is a schematic front view of the implantable active medical device illustrated in FIG. 2.
Figure 4:
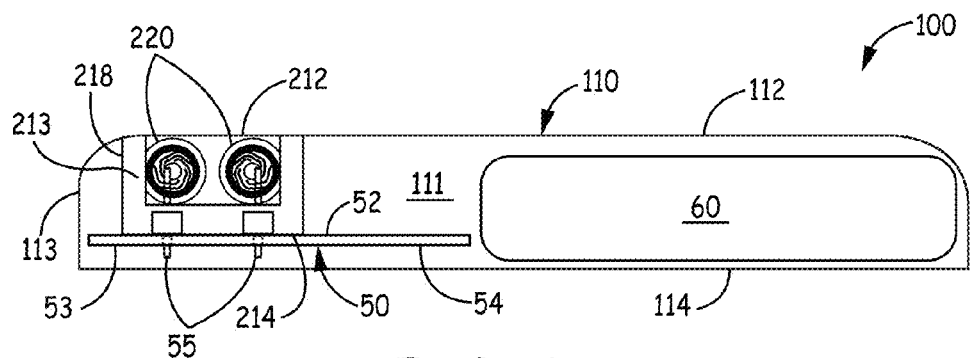
FIG. 4 is a schematic cross-sectional view of the implantable active medical device illustrated in FIG. 2 taken along line 4-4.
Figure 5:
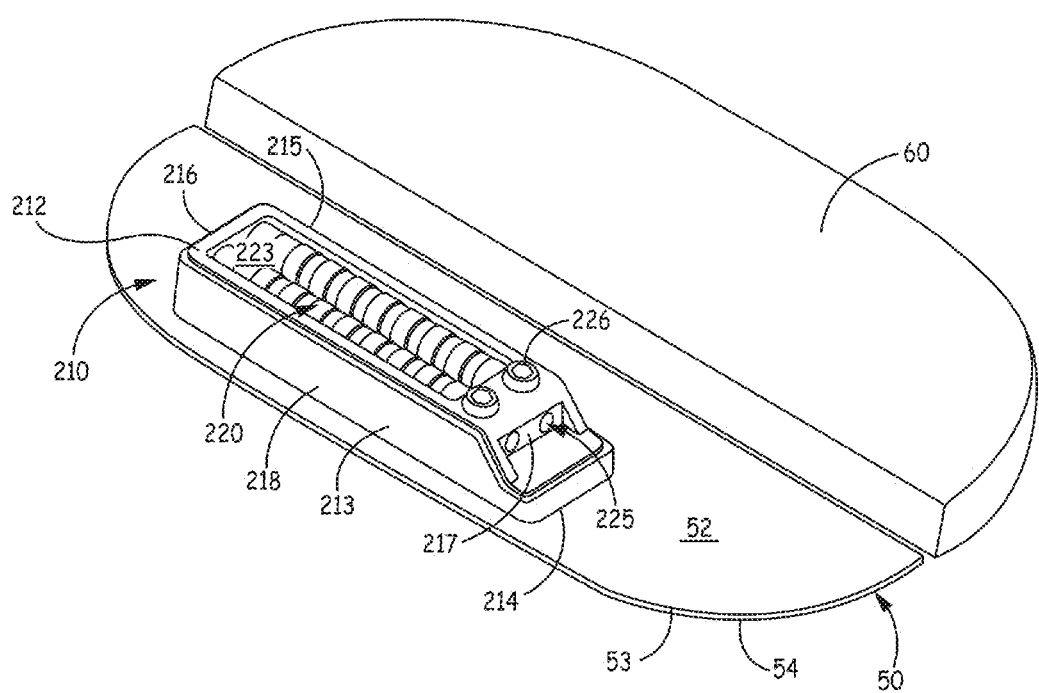
FIG. 5 is a schematic perspective view of the implantable active medical device illustrated in FIG. 2 without the hermetic housing.

FIG. 2 is a schematic perspective view of an illustrative implantable active medical device 100 with the elongate lead connector 210 recessed or embedded in a first major surface 112 of the hermetic housing 110. FIG. 3 is a schematic front view of the implantable active medical device 100 illustrated in FIG. 2. FIG. 4 is a schematic cross-sectional view of the implantable active medical device 100 illustrated in FIG. 2 taken along line 4-4. FIG. 5 is a schematic front view of the implantable active medical device 100 illustrated in FIG. 2 without the hermetic housing 110.

In many embodiments an implantable active medical device 100 includes a hermetic housing 110 defining an exterior surface and a hermetic cavity 111 of an implantable active medical device 100. The hermetic housing has a first major surface 112, an opposing second major surface 114 and a side surface 113 extending between the first major surface 112 and the opposing second major surface 114. An elongate lead connector 210 is recessed into the first major surface 112. The elongate lead connector 210 has a top surface 212 and a bottom surface 214 and a side surface 213 extending between the top surface 212 and the bottom surface 214. The top surface 212 forms only a portion of the first major surface 112.

In many embodiments an implantable active medical device 100 includes a hermetic housing 110 defining an exterior surface and a hermetic cavity 111 of an implantable active medical device 100. The hermetic housing 110 has a first major surface 112, an opposing second major surface 114 and a side surface 113 extending between the first major surface 112 and the second major surface 114. An elongate lead connector 210 is embedded into the first major surface 112. In some embodiments the elongate lead connector 210 is embedded into the side surface 113. As illustrated in FIG. 2 the elongate lead connector 210 forms a portion of the first major surface 112 and/or a portion of the side surface 113. A portion of the elongate lead connector 210 top surface 212 is removed to illustrate the two lead receptacles disposed in the lead connector 210, for ease of illustration. In many embodiments the elongate lead connector 210 is embedded into the first major surface 112 or the second major surface 114 and is co-extensive with or co-planar with only one of either the first major surface 112 or the second major surface 114.

The elongate lead connector 210 has a top surface 212 and a bottom surface 214 and opposing longitudinal side surfaces 215, 218 extending between the top surface 212 and the bottom surface 214. The lead connector 210 also has a closed end rear surface 216 extending between the top surface 212 and the bottom surface 214 and the opposing longitudinal side surfaces 215, 218, and an open end front surface 217 opposing the rear surface 216 and defining a lead aperture 225 and extending between the top surface 212 and the bottom surface 214 and the opposing longitudinal side surfaces 215, 218. The hermetic cavity 111 surrounds the opposing longitudinal side surfaces 215, 218 and the closed end rear surface 216. In other words, the opposing longitudinal side surfaces 215, 218 and the closed end rear surface 216 define at least a portion of the hermetic cavity 111.

In many embodiments, the top surface 212 of the elongate lead connector 210 is co-extensive with the first major surface 112 or the second major surface 114 of the hermetic housing 110 defining the hermetic cavity 111 of an implantable active medical device 100. In many embodiments, the top surface 212 of the elongate lead connector 210 is co-planar with the first major surface 112 or the second major surface 114 of the hermetic housing 110 defining the hermetic cavity 111 of an implantable active medical device 100. In many embodiments, the elongate lead connector 210 is embedded into the hermetic housing 110 exterior surface. The hermetic housing 110 defines a hermetic perimeter and the elongate lead connector 210 is disposed within the hermetic perimeter.

In many embodiments, the hermetic housing 110 exterior surface defines a rounded rectangular body, as illustrated in FIG. 2. In these embodiments, the first major surface 112 and the second major surface 114 can be parallel with each other and formed from two housing shells welded together along a single weld line. In some embodiments the elongate lead connector 210 is disposed between the first major surface 112 and the second major surface 114.

In many embodiments the implantable active medical device 100 includes electronics 50 disposed within the hermetic housing. Electronics can be any useful electronics such as a circuit board. A circuit board can include both a printed circuit board (often a rigid printed circuit board) and a flexible circuit (also known as a flex circuit), or a combination of a printed circuit board and a flex circuit. In many embodiments a electronics or circuit board 50 is electrically coupled to the elongate lead connector 210 via feedthroughs 55 and the electronics or circuit board 50 is disposed within the hermetic housing. The electronics or circuit board may also be rigidly fixed to the elongate lead connector by for example screws, clips, or other means. The hermetic housing 110 defines a hermetic cavity 111. In many embodiments the hermetic housing is a metallic shell.

The circuit board 50 has a top circuit major surface 52 and an opposing bottom circuit major surface 54 and a side surface 53 that extends between the top circuit major surface 52 and an opposing bottom circuit major surface 54. In many embodiments, the bottom surface 214 of the elongate lead connector 210 is parallel with, co-extensive with or contacts the top circuit major surface 52 of the circuit board 50. This configuration provides a secure connection between the circuit board 50 and the bottom surface 214 of the elongate lead connector 210. In some embodiments the feedthroughs 55 extend from the elongate lead connector 210 and through a thickness of the circuit board 50 or through both the top circuit major surface 52 and the opposing bottom circuit major surface 54. In many of these embodiments the feedthroughs 55 extend through the thickness of the circuit board 50 and are fixed to the bottom circuit major surface 54.

In many embodiments the elongate lead connector 210 is coupled to the circuit board 50 via feedthroughs 55 between the elongate lead connector 110 and the circuit board 50 as illustrated in FIG. 4 and FIG. 5. The electronics 50 generally control the active medical device. In some embodiments, the electronics 50 includes memory. The memory can be any magnetic, electronic, or optical media, such as random access memory (RAM), read-only memory (ROM), electronically-erasable programmable ROM, flash memory, or the like.

In many embodiments the implantable active medical device 100 includes a power source 60 disposed within the hermetic housing 110. The power source 60 can include a battery, for example disposed within a hermetic housing, shield or shell. The power source 60 can be electrically connected to the circuit board 50 via electrical connections such as soldering or welding. The power source 60 can be any useful battery or inductive coil. The power source can be mechanically fixed to the elongate lead connector 210 to minimize relative displacement between components.

In many embodiments, the lead connector 210 includes two or more electrically conducting contact rings 221 spaced apart by electrically insulating rings 222. The electrically conducting contact rings 221 and the electrically insulating rings 222 are aligned in axial alignment to form the two or more electrically conducting contact rings 221 provide electrical communication between the electronics or circuit board 50 and the therapy lead contact. The lead connector 210 provides a hermetic seal between the hermetic housing cavity 111 and the lead aperture 225.

The electrically conducting contact rings can be formed of any useful electrically conductive material. In many embodiments, the electrically conducting contact rings are formed of a metallic material such as, for example, titanium, stainless steel, MP35N, niobium, tantalum, platinum, and alloys or combinations thereof. In some embodiments, the electrically conducting contact rings are formed of a metallic material such as, for example, titanium.

The electrically insulating material 222 can be formed of any useful electrically flexible insulating material. In many embodiments the electrically insulating material 222 is liquid silicone rubber formed in such a configuration to provide electrical isolation between adjacent contact rings.

In some embodiments, a filtering capacitor is disposed between each electrically conducting contact rings 221 and the electronics 50. The filtering capacitor can effectively filter out undesirable electromagnetic interference (EMI) from the active medical device 100.

Embedding the lead connector 210 into the first major surface 112 of the active medical device housing 110 enables a direct electrical connection between the lead connector 210 and the electronics 50. In addition, the elimination of a traditional external lead connector block can reduce the size and volume of the implantable active medical device and can also reduce the number of parts and connections needed to assemble the implantable active medical device. Also, the method of attachment of the lead connector to the device housing is substantially simplified and the lead connector is isolated from external loading The illustrated lead connector 210 is an elongate member extending between a lead aperture 225 first or front open end 217 and a closed end or rear side or end cap 216, and having an inner surface defining an open lumen lead aperture 225. The open lumen lead aperture 225 or lead receptacle 225 is configured to accept one lead or lead extension, as described above, and electrically couple one or more lead contacts with one or more connector contacts 221 nested in the elongate body of the lead connector 210.

A retention member 226 such as for example, a set screw, can be disposed on the lead connector 210 adjacent to the open end 217 and can assist in mechanical retention of the lead disposed within the lead aperture 225.

In many embodiments, the circuit board 50 is directly coupled to the elongate lead connector 210 and the bottom surface 214 of the elongate lead connector 210 contacts a major surface 52 of the circuit board 50. In many of these embodiments, the bottom surface 214 of the elongate lead connector 210 is coextending and parallel with the major surface 52 of the circuit board 50 and the elongate lead connector 210 extends orthogonally away from the major surface 52 of the circuit board 50. In some of these embodiments, the entire bottom surface 214 of the elongate lead connector 210 contacts the major surface 52 of the circuit board 50.

In many embodiments the elongate lead connector is surrounded on all sides (opposing longitudinal side surfaces 215, 218, the closed end rear surface 216 and the bottom surface 214), except for the top surface 212 and an open end side surface 217 defining a lead aperture 225, by the hermetic housing exterior surface 110, as illustrated in FIG. 2.

In some illustrative embodiments, the first major surface 112 defines a ledge surface 115 that is recessed from the first major surface 112 and the ledge surface 115 is coextensive with the bottom surface 214 of the elongate lead connector 210. The ledge surface 115 can form a ledge feature on the first major surface 112 and the ledge feature exposes an open end side surface 217 defining a lead aperture 225 of the elongate lead connector 210 to allow a lead to be inserted into the lead aperture 225.

In some embodiments, a portion of the top surface 212 is transparent to allow for visual confirmation that a lead is engaged within the elongate lead connector 210. The transparent element 223 can be formed of any useful transparent material such as glass or polymer and the like.

Thus, embodiments of the IMPLANTABLE DEVICE WITH SHIELD INTEGRATED LEAD CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device comprising:
a hermetic housing defining an exterior surface and a hermetic cavity of an implantable active medical device, the hermetic housing having a first major surface, an opposing second major surface and a side surface extending between the first major surface and the second major surface;
an elongate lead connector recessed into the first major surface, and the elongate lead connector extends parallel to the first major surface and the second major surface, the elongate lead connector having a top surface and a bottom surface and a side surface extending between the top surface and the bottom surface; the top surface forming only a portion of the first major surface, and the top surface being co-planar with the first major surface.

2. The implantable active medical device according to claim 1, further comprising a circuit element disposed within the hermetic cavity and directly coupled to the elongate lead connector and the bottom surface of the elongate lead connector contacts a major surface of the circuit element.

3. The implantable active medical device according to claim 2, wherein the bottom surface of the elongate lead connector is coextending and parallel with the major surface of the circuit element and the elongate lead connector extends orthogonally away from the major surface of the circuit element.

4. The implantable active medical device according to claim 2, wherein the entire bottom surface of the elongate lead connector contacts the major surface of the circuit element and the circuit element is a circuit board.

5. The implantable active medical device according to claim 1, wherein the elongate lead connector is disposed between the first major surface and the second major surface.

6. The implantable active medical device according to claim 1, wherein the elongate lead connector is surrounded on all sides, except for the top surface and an open end side surface defining a lead aperture, by the hermetic housing exterior surface.

7. The implantable active medical device according to claim 1, further comprising a power source disposed within the hermetic cavity.

8. The implantable active medical device according to claim 1, wherein the first major surface defines a ledge surface that is recessed from the first major surface and the ledge surface is coextensive with the bottom surface of the elongate lead connector.

9. The implantable active medical device according to claim 8, wherein the ledge surface forms a ledge feature on the first major surface and the ledge feature exposes an open end side surface defining a lead aperture of the elongate lead connector to allow a lead to be inserted into the lead aperture.

10. The implantable active medical device according to claim 1, wherein a portion of the top surface is transparent to allow for visual confirmation that a lead is engaged within the elongate lead connector.

11. An implantable active medical device comprising:
a hermetic housing defining an exterior surface and a hermetic cavity of an implantable active medical device, the hermetic housing having a first major surface, an opposing second major surface and a side surface extending between the first major surface and the second major surface;
an elongate lead connector embedded into the first major surface, and the elongate lead connector extends parallel to the first major surface and the second major surface, the elongate lead connector having a top surface and a bottom surface and opposing longitudinal side surfaces extending between the top surface and the bottom surface, the top surface being co-planar with the first major surface, and a closed end rear surface extending between the top surface and the bottom surface and the opposing longitudinal side surfaces, and an open end front surface opposing the rear surface and defining a lead aperture and extending between the top surface and the bottom surface and the opposing longitudinal side surfaces;
wherein the hermetic cavity surrounds the opposing longitudinal side surfaces and the closed end rear surface.

12. The implantable active medical device according to claim 11, wherein the hermetic housing surrounds the opposing longitudinal side surfaces and the closed end rear surface.

13. The implantable active medical device according to claim 11, wherein top surface of the elongate lead connector is coextensive with the first major surface.

14. The implantable active medical device according to claim 11, further comprising a circuit board disposed within the hermetic cavity and directly coupled to the elongate lead connector, the circuit board has a top circuit major surface and an opposing bottom circuit major surface, and the bottom surface of the elongate lead connector contacts the top circuit major surface of the circuit board.

15. The implantable active medical device according to claim 14, wherein the bottom surface of the elongate lead connector is coextending and parallel with the top circuit major surface of the circuit board and the elongate lead connector extends orthogonally away from the top circuit major surface of the circuit board.

16. The implantable active medical device according to claim 14, wherein the entire bottom surface of the elongate lead connector contacts the top circuit major surface of the circuit board.

17. The implantable active medical device according to claim 11, further comprising a power source disposed within the hermetic cavity.

18. The implantable active medical device according to claim 11, wherein the first major surface defines a ledge surface that is recessed from the first major surface and the ledge surface is parallel to the first major surface and coextensive with the bottom surface of the elongate lead connector.

19. The implantable active medical device according to claim 18, wherein the ledge surface forms a ledge feature on the first major surface and the ledge feature exposes the open end front surface of the elongate lead connector to allow a lead to be inserted into the lead aperture.

20. The implantable active medical device according to claim 11, wherein a portion of the top surface is transparent to allow for visual confirmation that a lead is engaged within the elongate lead connector.

* * * * *